(12) United States Patent
Musat

(10) Patent No.: US 10,670,593 B2
(45) Date of Patent: *Jun. 2, 2020

(54) MATRIX FOR RECEIVING A TISSUE SAMPLE AND USE THEREOF

(71) Applicant: Leavitt Medical, Inc., Orem, UT (US)

(72) Inventor: Sorin Musat, Bucharest (RO)

(73) Assignee: Leavitt Medical, Inc., Lehi, UT (US)

( * ) Notice: Subject to any disclaimer, the term of this patent is extended or adjusted under 35 U.S.C. 154(b) by 174 days.

This patent is subject to a terminal disclaimer.

(21) Appl. No.: 15/853,251

(22) Filed: Dec. 22, 2017

(65) Prior Publication Data
US 2018/0120308 A1 May 3, 2018

Related U.S. Application Data

(62) Division of application No. 14/129,377, filed as application No. PCT/RO2012/000017 on Jun. 28, 2012, now Pat. No. 9,851,349.

(60) Provisional application No. 61/502,513, filed on Jun. 29, 2011.

(51) Int. Cl.
*G01N 33/543* (2006.01)
*G01N 1/36* (2006.01)
*G01N 1/30* (2006.01)
*G01N 1/42* (2006.01)

(52) U.S. Cl.
CPC ........... *G01N 33/5436* (2013.01); *G01N 1/36* (2013.01); *A61K 2300/00* (2013.01); *G01N 1/30* (2013.01); *G01N 1/42* (2013.01)

(58) Field of Classification Search
CPC ........ A61K 2300/00; A61K 8/64; A61K 8/19; A61K 8/042; A61K 47/02; A61K 8/922; A61K 8/98; A61K 9/282
See application file for complete search history.

(56) References Cited

U.S. PATENT DOCUMENTS

| 5,127,537 | A | 7/1992 | Graham | |
| 9,851,349 | B2 * | 12/2017 | Musat | G01N 1/36 |
| 2014/0135236 | A1 | 5/2014 | Musat | |

FOREIGN PATENT DOCUMENTS

WO 2006039396 A2 4/2006

OTHER PUBLICATIONS

Encyclopaedia Britannica, Paraffin wax, available at http://www.britannica.com/science/paraffin-wax (last visited Jul. 11, 2017).
"Multitissue array review: a chronological description of tissue array techniques, applications and procedures", Egualuz et al., Pathology, Research and Practice, vol. 202, No. 8, Jan. 1, 2006, p. 561.
Eguiluz et al. Multitissue array review: a chronological description of tissue array techniques, applications and procedures. Pathology—Research and Practice. 2006;202:561-568.
Jones et al. Agar-gelatin for embedding tissues prior to paraffin processing. BioTechniques. 2007;42(5):569-570.
International Search Report issue in PCT Application No. PCT/RO2012/00017, dated Dec. 10, 2012.
UCSD. Recommended protocols for preserving tissues for histopathologic examination. UCSD. 2010; 1-11.
Meat. What is meat? www.exploratorium.edu. 2009;1-2.
Omar SH. Oleuropein in olive and its pharmacological effects. Scientia Pharmaceutica. 2010;78:133-154.
"Methods in Laboratory Investigation the Multitumor (Sausage) Tissue Block: Novel Method for Immunohistochemical Antibody Testing", H. Battifora, Laboratory Investigation, Nature Publishing Group, The United States and Canadian Academy or Pathology, Inc., vol. 55, No. 2, Jan. 1, 1986, pp. 244-248.
"Tissue microarrays for high-throughput molecular profiling of tumour specimens", Kononen et al., Nature Medicine, Nature Publishing Group, New York, NY, US, vol. 4, No. 7, Jul. 1, 1988, pp. 844-847.
"Inhibition of Apoptosis After Ischemiareperfusion in Rat Myocardium by Cycloheximide", Sorin Musat-Marcu, et al. Journal of Molecular and Cellular Cardiology, Academic Press, GB, vol. 31, No. 5, May 1, 1999, pp. 1073-1082.

* cited by examiner

*Primary Examiner* — Lynn Y Fan
(74) *Attorney, Agent, or Firm* — FisherBroyles, LLP

(57) ABSTRACT

A custom-made matrix suitable for receiving a tissue sample is described, as well as the use thereof to obtain a multiplex histological preparation. The disclosure also relates to a multiplex biopsy array comprising tissue and/or cell samples arranged in a matrix material and to a method for the preparation of a multiplex biopsy array. Methods for preparing blocks of matrix material to be used in multiplex biopsy arrays are also described, as well as methods for loading biopsy samples in the blocks, and methods for treating and processing the blocks to form biopsy arrays. The biopsy arrays made using the block of matrix material can be used to prepare sections and slides for histological procedures, including quantitative analyses and parallel processing.

7 Claims, 9 Drawing Sheets

FIG. 1C
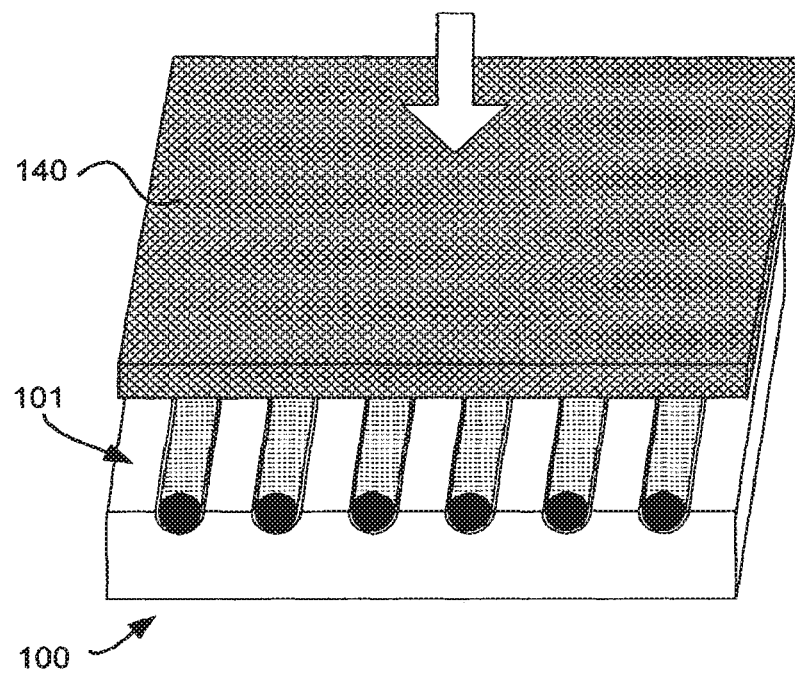
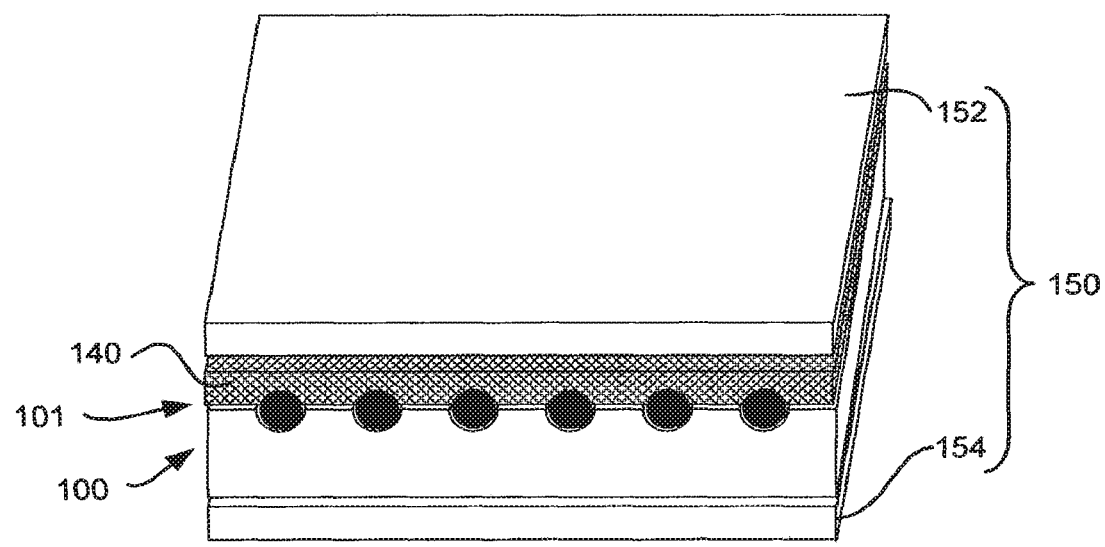
FIG. 1D

FIG. 1E
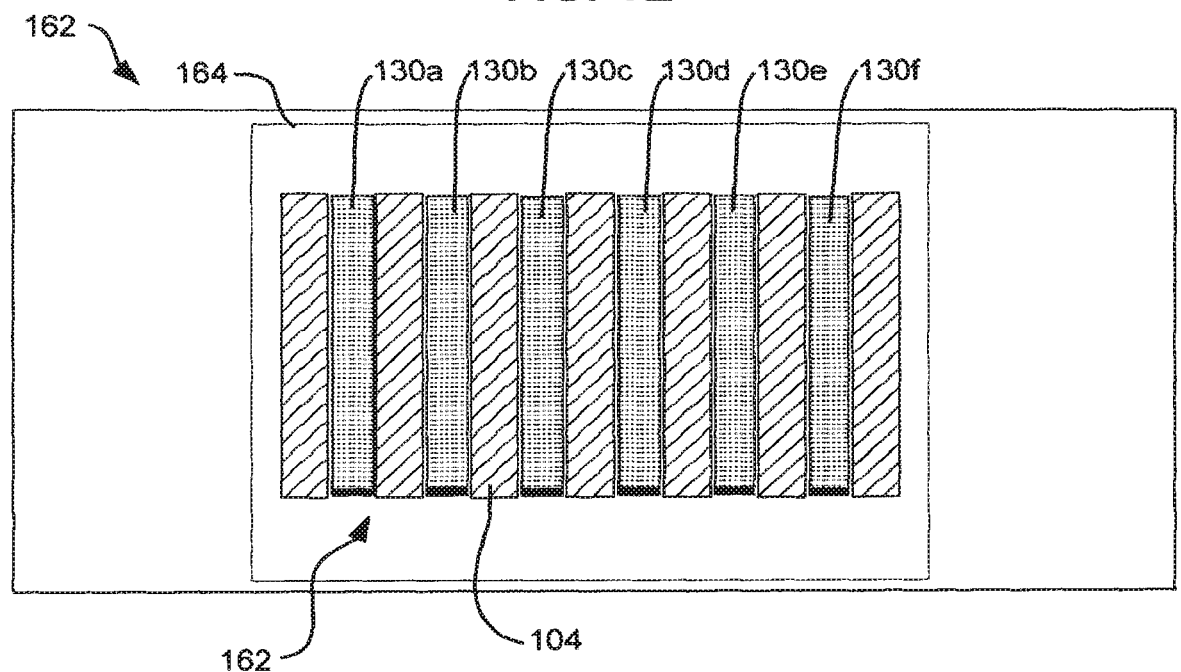
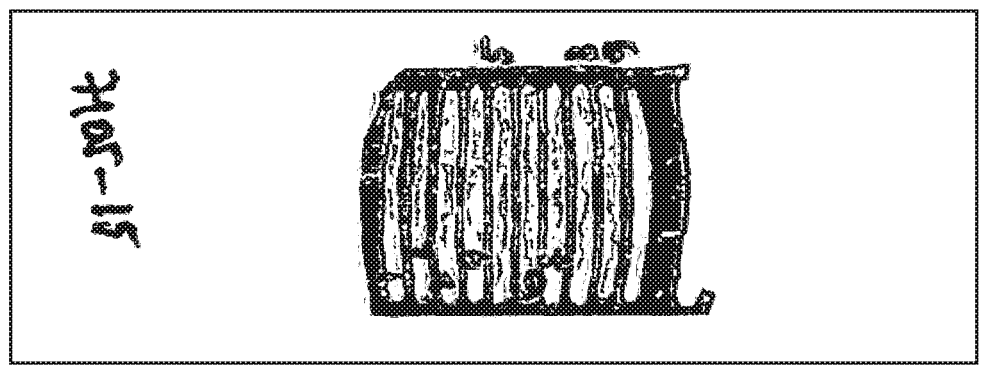
FIG. 1F

MATRIX FOR RECEIVING A TISSUE SAMPLE AND USE THEREOF

CROSS-REFERENCE TO RELATED APPLICATIONS

This application is a divisional of U.S. patent application Ser. No. 14/129,377, filed Dec. 26, 2013, which will issue as U.S. Pat. No. 9,851,349 on Dec. 26, 2017, which is a national phase entry under 35 U.S.C. § 371 of International Patent Application PCT/RO2012/000017, filed Jun. 28, 2012, designating the United States of America and published as International Patent Publication WO 2013/002661 A1 on Jan. 3, 2013, which claims the benefit of U.S. Provisional Patent Application Ser. No. 61/502,513, filed Jun. 29, 2011, titled "MATRIX AND METHOD FOR THE PREPARATION OF MULTIPLEX BIOPSY ARRAYS," the disclosure of each of which is hereby incorporated herein in its entirety by this reference.

TECHNICAL FIELD

The disclosure relates to a custom-made matrix suitable for receiving a tissue sample and to the use thereof to obtain a multiplex histological preparation. The disclosure also relates to methods for preparing blocks of matrix material to be used in constructing multiplex biopsy arrays, methods for loading tissue samples in the blocks, and methods for treating and processing the blocks and arrays in preparation for analysis.

BACKGROUND

The tissue sample may result from a needle biopsy (sometimes referred to as tru-cut biopsy), fine needle aspirate or an explant. A needle biopsy is a common medical test involving the removal, with the aid of a hollow needle, of a representative sample of cells or tissues from a living subject for examination to determine the presence or extent of a disease. Fine needle aspiration (FNA) is a diagnostic procedure sometimes used to investigate superficial (just under the skin) lumps or masses or hollow organs. According to this technique, a thin hollow needle is inserted into the mass for sampling of cells that, after being stained, will be examined under a microscope. A biological sample harvested from a piece or pieces of tissue is called an "explant." The explant and/or biopsy sample is subjected to treatments, such as fixation, sectioning and staining, and then examined by a pathologist. The tissue sample can also be analyzed chemically. For the sake of brevity, the term "biopsy" will be used throughout this application with the understanding that it refers to tru-cut biopsies as well as to fine needle aspirates and free-form explants.

Patterned biopsies play a major role in the early detection of various types of cancer (i.e., prostate, breast, thyroid, skin, intestine, lung, stomach, etc.). Maintaining site-specific information regarding individual biopsy cores is of critical importance. While individual processing of biopsies by conventional methods is prohibitively expensive, current methods of parallel processing (tissue microarrays, color coding, multi-compartment cassettes, etc.) are either not accurate, cumbersome, or both.

A standard biopsy method uses a needle to remove a biopsy sample for examination. A tru-cut needle biopsy removes small but solid samples of tissue using a hollow "core" needle. In a core biopsy, a small cylindrical sample of tissue is removed preserving the histological architecture of the tissue's cells. This is important when dealing with biopsies (e.g., prostatic, breast) where one has to report the percentage of malignant tissue. The samples are small, and fragile, and tend to curl during processing, making preparation of the sample for examination difficult.

In the United States, there are approximately 1 million patients requiring biopsies for early diagnosis of prostate cancer. On average, 10 to 21 biopsy samples are taken per patient with suspicion of prostate cancer and their precise location has to be recorded. In some cases "prostate mapping"/saturation biopsies are performed (up to 60 to 80 biopsy samples per patient). Utilizing the standard biopsy technique (in which one, or maximum two, biopsies are processed at a time) results in a huge number of paraffin blocks, requiring a large number of sections and slides, high expenditures in terms of consumables, manpower for processing and time spent by the pathologists for interpreting the slides. Moreover, in order to provide the required 3-D reconstruction analysis of malignancy, it is very important to record and map the location of the sections relative to the original biopsy sample.

Traditionally, when dealing with biopsy samples, the recommended approach is to process the samples by embedding individually in a supporting material such as a paraffin block. The paraffin blocks containing the individual samples are then sectioned with a microtome to produce thin sections that will be placed on a microscope slide, stained as needed and examined under a microscope. When sectioning the paraffin blocks, one runs the risk of not intercepting the tissue sample and/or losing too much of the sample before a (quasi) complete section is produced. For example, when dealing with prostate biopsies, current recommendations require three different sections ("step" sections, or "levels") taken at approximately 50 microns apart. Usually, two to three additional sections (unstained) are saved at every step/level for further staining, if required by the pathologist. Sufficient material should remain in the block for further study as well as for archiving, litigation, etc. Because of the scarcity of the material in the sample, only adhesive-coated slides (i.e., 10 to 20 times more expensive than regular variety) are employed, to minimize the risk of accidentally losing the sections during staining.

In recent years, trans-rectal ultrasound-guided (TRUS) systematic needle biopsy has emerged as a new gold standard in prostate cancer diagnosis, to such an extent that statistical performance values (sensitivity, specificity, positive and negative predictive values) of all other diagnostic tests, like digital rectal examination (DRE) or prostate-specific antigen (PSA) are computed according to the outcome of biopsy examination. A computerized model of the prostate, including mapped sections from 159 whole-mount radical prostatectomy specimens, subjected to systematic histopathology examination showed that the six-core biopsy technique fails to identify 26.8% of the tumors. Even on repeated examination, this method resulted in failure of tumor identification in 27 of 118 prostate cancer patients, equivalent to 23% of total cases demonstrated following radical prostatectomy. From a plethora of recent studies comparing results of different biopsy strategies regarding the number and location of cores, the emerging consensus, based on clinical trials, ex vivo biopsy approaches, as well as various computer simulations and mathematical models, is to take at least ten biopsy cores, focusing the biopsies laterally at the base, mid-gland, and apex of the prostate, with mid-lobar biopsy cores at the base and apex, and adjusting the number of cores taken according to prostate volume and age of the patient. Some investigators advocate even more aggressive biopsy schemes, with more than 12 cores, up to a saturation biopsy (>20 cores), especially on repeat biopsies, reporting even higher cancer detection rates. However, despite the obvious need for multiple biopsy cores per patient, due to high expenses and limited resources, the number of biopsies taken and sections prepared per patient is typically reduced to the minimum required for an acceptable precision of the diagnosis and/or the maximum resources available within an institution. Thus, a system for rapid, cost-effective preparation and analysis of multiple cores at multiple levels is needed.

An array is an organized fashion of multiple tissue and/or cell samples that can be used in various histological techniques including topographical staining, (immuno)histochemistry, immuno-fluorescence, and in situ hybridization. Tissue and cell arrays are powerful tools because they allow simultaneous screening of numerous tissue or cell samples. The value of this type of technology is that testing can be done on many samples in a timely manner with consistency. This allows for high-throughput histological screening or analysis.

There are a number of methods that describe the construction of tissue or cell arrays including: the "sausage" method (see Battifora, "The multitumor (sausage) tissue block: novel method for immunohistochemical antibody testing" (1986) *Lab. Invest.* 55:244; and U.S. Pat. No. 4,820,504); paraffin-to-paraffin transfer methods (see Kononen et al., "Tissue microarrays for high throughput molecular profiling of tumor specimens" (1998) *Nature Medicine* 4(7):844-847); the "honeycomb" method (see K. Petrosyan and M. F. Press, "Multispecimen tissue blocks in pathology: an improved technique of preparation" (1997) *Lab. Invest.* 77(5):541-542); and the use of liver as a recipient matrix for the array (see Musat-Marcu et al., "Inhibition of apoptosis after ischemia-reperfusion in rat myocardium by cycloheximide" (1999) *J. Mol. Cell. Cardiol.* 31:1073-1082). Also see U.S. Pat. No. 4,647,543; Miller and Groothius, *A.J.C.P.* 96:228-232; Sundbland, *A.J.C.P* 102:192-193; Patent Application No. WO1999IUS9912537; Patent Application No. PCT/US99/04000; Patent Application No. WO1999/WO0004001 and U.S. patent application Ser. No. 1987000110818.

The "sausage" technique involves combining multiple tissue samples from a deparaffinized block into a single composite "sausage" held together with a wrapper of intestinal casing. The multiple tissue sausages are re-paraffinized, sectioned and then mounted on slides. This procedure allows hundreds of tissue samples to be tested simultaneously. Even though this approach is valuable, it has a number of inherent disadvantages. For instance, the technical effort and time required to prepare the composite sausage causes difficulties. In addition, the need to de-paraffinize and re-paraffinize the tissue samples could lead to a loss of antigens. There are problems in maintaining the spatial relationships among the different tissue samples and working with small specimens such as cells, because of the flexible nature of the intestinal casing.

There have been a number of other paraffin-to-paraffin or double-embedding techniques that have evolved to fix some of the problems with the "sausage" technique (see U.S. Pat. Nos. 4,914,022 and 5,002,377). A common multi-specimen technique involves the preparation of standard paraffin blocks of tissue specimens where core samples are then removed from these blocks and re-embedded into a recipient paraffin block to create the tissue array (see U.S. Pat. No. 4,914,022). This technique can be used to test multiple tissue samples from multiple sources at the same time. In addition, it is possible to take a tissue chip, which is a thin section of the tissue array, and parallel process a number of samples at the same time with a variety of stains or molecular markers. The problem with this technique is that in order to prepare the tissue chips, custom-built equipment is required, which includes a computer-controlled micro-stage. In addition, the recipient paraffin block cannot be cut unless the adhesive tape technique is employed. The adhesive tape technique is expensive and time-consuming, and because the cut sections require special treatments before staining, there is a risk of compromising the accuracy of many applications. Another problem with paraffin-to-paraffin techniques is that the recipient paraffin block cannot cut efficiently and, thus, a number of sections are lost. Also, serial sectioning of the recipient block to produce ribbons is virtually impossible. Another limitation of this technique is that the tissue samples must be paraffinized and then re-paraffinized, thus, it is not possible to use fresh samples to create the microarray and antigens might be lost in the process. This technique can also be used to construct cell arrays; however, the same disadvantages exist as found when constructing tissue arrays (see M. Cottler-Fox and C. H. Fox, *J. Infect. Dis.* (1991), 164:1239-1240).

The "honeycomb" technique to create tissue arrays has the advantage of being able to employ fresh or fixed tissue without prior embedding. This technique uses a multichambered mold ("honeycomb") made with plastowax. Small tissue specimens are placed in the equal-sized spaces of the mold, and then the molds are embedded with PARA-PLAST®. The multi-specimen tissue blocks are processed, sectioned and stained using conventional methods. The problem with this technique is that precise orientation of the individual samples is not possible. As a result, its applications are very limited and, as such, it is not widely used. Like all previous methods, it requires infiltration followed by embedding, for example, in paraffin.

Liver tissue has previously been proposed as a support for facilitating sectioning of tissue samples (see, e.g., Manfred Gabe, "Histological Techniques," p. 125 (Springer-Verlag 1976), and Musat-Marcu et al., "Inhibition of apoptosis after ischemia-reperfusion in rat myocardium by cycloheximide," *J. Mol. Cell. Cardiol.* 31:1073-1082 (1999). Tissue and cell arrays can be constructed using liver as the recipient matrix. This technique works for fixed, fresh, or paraffinized tissue or cell samples. The problems with this technique include the low efficiency in generating the required matrices and the occasional hidden "defects" in the liver matrix, such as biliary ducts, blood vessels and collagen septa that results in a loss of samples. In addition, there is possible cross-reactivity between the matrix and biopsy samples.

Thus, although tissue arrays and cell arrays are powerful tools to allow simultaneous screening of numerous tissue or cell samples, there are no simple methods for creating arrays using core biopsy sample or free-form explants.

BRIEF SUMMARY

Embodiments of the present disclosure provide an inexpensive and precise method for parallel processing of prostate core biopsies that generates high yields and minimal losses while maintaining site-specific information regarding biopsy cores.

In one aspect, the present disclosure relates to a custom-made matrix suitable for receiving a tissue sample and to the use thereof to obtain a multiplex histological preparation. The disclosure also relates to methods for preparing blocks of matrix material for preparing multiplex biopsy arrays, methods for loading biopsy samples in the blocks, and methods for treating and processing the blocks and arrays in preparation for analysis.

In another aspect, the present disclosure provides a tissue matrix employed as a recipient matrix for biological samples, such as tissue and/or cell sample(s). In one embodiment, the disclosure provides a matrix that can be used for receiving at least one biopsy sample, wherein the biopsy sample is of a different origin from the tissue matrix. In addition, the disclosure provides a tissue matrix that can be used to construct a biopsy array.

In another embodiment, the disclosure also concerns a method for preparing a biopsy sample and a recipient matrix for use in the disclosure, and to a method for constructing a biopsy array using the matrix. The disclosure includes the use of the biopsy array or embedded biological sample, for instance, in histological procedures. In one aspect, the disclosure provides a histological preparation comprising a recipient matrix of the disclosure and a tissue and/or cell sample. In a further embodiment, the recipient matrix can be used in the production of single or multi-specimen/multi-use preparations. In a preferred embodiment, the recipient matrix is comprised of processed animal tissue. For the purposes of this specification, animal tissue is meant to comprise, inter alia, porcine tissue, avian tissue, fish tissue, etc.

In another embodiment, the disclosure relates to a processed animal tissue matrix that can be used to embed a biological sample or construct a tissue and/or cell array. The processed animal tissue used in the matrix consists of a suitable blend of proteins, fat and water to produce a matrix with minimal shrinking and good cutting properties.

In another embodiment, the disclosure relates to the use of SPAM® processed pork to construct the processed animal tissue matrix. The labeled ingredients in the classic variety of SPAM® are chopped pork shoulder meat, with ham meat added, salt, water, modified potato starch as a binder, and sodium nitrite as a preservative. An advantage of SPAM® processed meat is that it allows the matrix and tissue samples to be readily distinguished when biopsy samples are embedded therein. In addition, the size and shape of the matrix can be varied and, thus, allows flexibility in preparing the biopsy array.

In another embodiment, the disclosure provides a method for preparing the processed animal tissue for use in creating biopsy arrays. The processed animal tissue can be treated using known histological techniques. The processed animal tissue can be fresh, fixed or embedded. Receptacles are formed in the processed animal tissue matrix, and tissue biopsies or cells are placed therein, with or without the aid of a vacuum, to create the matrix.

In another embodiment, the disclosure provides a method of treating and obtaining a biological sample, such as a biopsy sample to be used in the matrix to create the array. An advantage of this disclosure is that small samples are as easily handled as larger samples. Thus, it is possible to use tissue samples or cell samples in the array. In addition, the biopsy samples can be in a variety of preparative forms, including fresh, fixed or paraffin-embedded, and, thus, the problems of prior methods that require each tissue sample to be paraffinized and re-paraffinized are avoided. A wide assortment of sources can be used as samples, such as normal organs/tissues, tumors, blood, bodily fluids or secretions, primary cell cultures and cell lines.

In another embodiment, the disclosure provides biopsy arrays made using the processed animal tissue matrix. The biopsy arrays that are constructed using the processed animal tissue matrix are flexible in their design. The array may be composed of tissues or cells or a combination of both tissues and cells. The size and shape of the array can be varied to support different sizes and shapes of biopsy samples. The arrays can be custom designed to compare different samples from a single species, the same cell or tissue type from different species, or the same cell or tissue type from the same species at different developmental times. Advantages of this disclosure include ease of sectioning the matrix and minimal shrinkage.

In another embodiment, the disclosure provides a method for preparing the biopsy arrays. The processed animal tissue matrix is preferably in a similar or subsequent preparative stage as the tissue and/or cell sample before the sample is arranged in the processed animal tissue matrix to create the biopsy array. In one embodiment, the cell or tissue is arranged in the receptacle in the processed animal tissue matrix with or without the aid of a low vacuum. A thin layer of additional processed animal tissue matrix, which is preferably in a similar preparative stage as the original processed animal tissue matrix, can be used as a lid to cover the receptacle when needed. The biopsy array can then be processed using known histological techniques. The present method creates a biopsy array that can be easily cut to create consistent duplicate samples or arrays for analysis or other purposes. Therefore, unlike other methods, it can be used efficiently for parallel analysis or quantitative analysis of various biopsy samples. This new method overcomes the disadvantages noted above in the construction and use of biopsy arrays. This method is inexpensive and avoids the problems of other methods.

In another embodiment, the disclosure relates to a matrix material for preparing multiplex biopsy arrays comprising the matrix material. The disclosure also relates to methods for preparing blocks of matrix material for preparing multiplex biopsy arrays, methods for loading biopsy samples in the blocks, and methods for treating and processing the blocks and arrays in preparation for analysis.

In another embodiment, the disclosure includes a histological preparation comprising a matrix suitable for receiving a biopsy sample in combination with at least one biopsy sample arranged in the matrix, wherein the biopsy sample is of a different origin from the tissue matrix.

In another embodiment, the disclosure provides a method for preparing a histological preparation comprising a matrix material suitable for receiving a biopsy sample in combination with at least one biopsy sample arranged in the matrix, wherein the biopsy sample is of a different origin from the matrix material. The method includes the following preparative steps: fixation, dehydration, infiltration with a transitional solvent, and embedding in a binding agent when the biopsy arranged therein is in a similar or subsequent preparative state as the matrix material.

In another embodiment, the disclosure provides a method for preparing a histological preparation comprising a matrix material suitable for receiving a biopsy sample in combination with at least one biopsy sample arranged in the matrix, wherein the biopsy sample is of a different origin from the matrix material. The method includes preparing a frozen sample without fixation, dehydration, clarification or embedding.

In another embodiment, the disclosure provides methods for use of the biopsy arrays. The biopsy arrays allow for simultaneous histological testing of multiple individual biopsy samples on a single slide. Uses of the disclosure include creating sections and slides of a variety of biopsy samples. These sections or slices can be used with chemical or biological stains, histochemistry, genetic probes, and other reagents.

In one embodiment, the biopsy array is paraffin-embedded. The processed animal tissue array is flipped over in a base mold, and the paraffin block is prepared using known procedures. The block can be cut and used according to known histological techniques. In one embodiment, the block is cut into sections. The technique of sectioning is known to persons skilled in the art.

In another embodiment, the disclosure provides a use of the matrix to create biopsy arrays that, in turn, can be used for histological purposes. Histological purposes are known to persons skilled in the art. Such purposes include immunochemistry, immuno-fluorescence, in situ hybridization, fluorescence in situ hybridization and the use of genetic probes, chemical and biological reagents and stains using techniques known to those skilled in the art. In addition, the disclosure can be used to create slides, sections and tissue banking systems, which can be used in histological and quantitative analyses.

In one embodiment, a tissue biopsy array created using the processed animal tissue matrix has less variation in results because the samples are treated simultaneously. The present disclosure has a number of advantages including greatly enhanced efficiency and speed for tissue testing; greatly decreased cost for multiple tissue testing; great economies in the use of tissue samples, reagents and testing materials; great flexibility and ease of constructing biopsy arrays; lack of need for deparaffinization and re-embedding; ability to use tissues or cells as sources of samples for the array; and the ability to use fresh, fixed or paraffinized biopsy sources. In one embodiment, it also enables one to obtain serial sections (ribbons), for instance, as thin as 2 μm. In another embodiment, a biopsy array can be produced in less than 8 hours, more preferably between 8 and 24 hours. When using banked tissue (transitional solvent), an arrayed block can be generated within 3 hours for paraffin embedding, and in 10 to 15 minutes for frozen preparations.

This disclosure includes a matrix material that can be used to reliably and inexpensively create biopsy arrays. The disclosure also relates to the methods of constructing the biopsy arrays using the matrix material and the use of the arrays in histological procedures. In a preferred embodiment, the matrix material is comprised of processed animal tissue. In one embodiment, the disclosure provides the use of processed animal tissue as a recipient matrix of a tissue and/or cell sample for histological purposes.

Thus, the present disclosure provides a new matrix material and methods for preparing multiple biopsy arrays.

BRIEF DESCRIPTION OF THE DRAWINGS

FIG. 1C illustrates the application of a sponge to the matrix block of FIG. 1A.

FIG. 1D illustrates the matrix block of FIG. 1A and sponge of FIG. 1C in combination with a tissue cassette.

FIG. 1E illustrates a slide prepared from a section of the matrix block and biopsy samples of FIG. 1A according to an embodiment of the disclosure.

FIG. 1F is a picture of a sample slide prepared utilizing the matrix block of this disclosure.

DETAILED DESCRIPTION

Figure 1A:
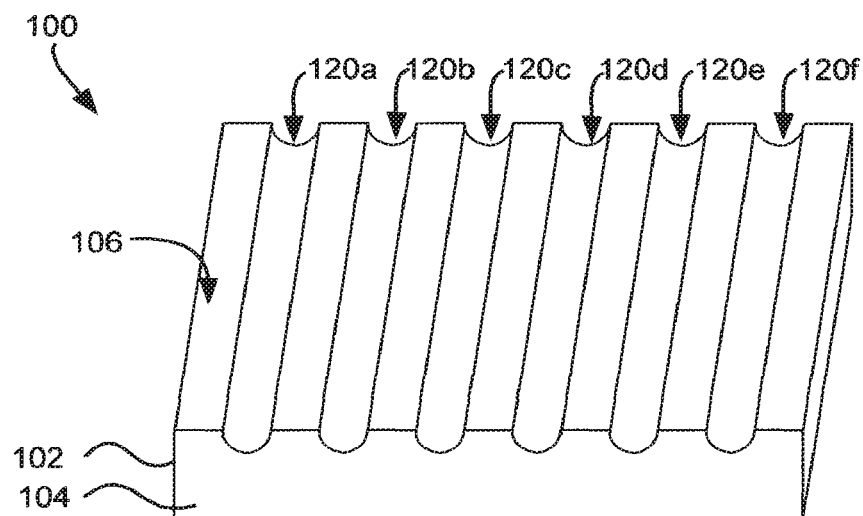
FIG. 1A is a perspective view of a matrix block for receiving biopsy samples according to an embodiment of the disclosure.

This disclosure refers to a histological preparation comprising a matrix material suitable for receiving a tissue and/or cell sample to the matrix material itself and to a tissue/cell array comprising at least one tissue and/or cell sample arranged in the matrix. In one embodiment, the tissue and/or cell sample is of a different origin from the matrix material.

A histological preparation is known to persons skilled in the art. It includes blocks, sections and slides of various tissue and/or cell samples prepared using histological techniques or practices. There are many histological techniques known to persons skilled in the art. In one embodiment, the following histological technique is used to create a histological preparation of a biopsy sample. A biopsy sample is obtained and then prepared using the ensuing preparative stages preferably in this order: fixation, dehydration, if required, infiltration with a transitional solvent, and embedding in a binding agent. The tissue can then be sectioned as desired. A person skilled in the art would understand that variations of such method and other histological preparation techniques suitable for use in the disclosure are available. Further, such a person would understand that depending on the tissue, cell or use thereof, certain steps may be added or omitted. One of the advantages of this disclosure over the prior art is that the same technology could be used for frozen preparations, where no fixation, dehydration, clarification or embedding is employed.

"Fixation" as used herein refers to treating the sample with a fixative. Fixatives are well known to persons skilled in the art. Fixatives include physical agents such as freezing in liquid nitrogen, dehydration, or microwaving, or chemical agents such as acids (e.g., picric, nitric, acetic), alcohols (e.g., ethanol), aldehydes (e.g., formaldehyde, glutaraldehyde) and others (e.g., mercuric chloride) or a combination thereof (e.g., formaldehyde/ethanol mixtures). Fixatives usually operate by denaturing, coagulating or cross-linking the proteins found in the biological samples. Fixatives may work by stopping all live processes. They may prevent decay, maintain the spatial distribution of constituents or allow and/or facilitate the eventual staining of the resulting sections. Persons skilled in the art would be familiar with suitable fixatives for use in this disclosure.

Dehydration is a process known to persons skilled in the art. One method of dehydration is infiltrating the sample with graded concentrations of a dehydrating agent such as ethanol, such as at 50%, then 70%, then 90% and finally 100% ethanol. A person skilled in the art would know that many other dehydrating agents and methods of dehydration would be suitable for this disclosure.

Transitional solvents are known to persons skilled in the art. They are commonly used after the dehydration step but before the embedding step. A transitional solvent is selected on the basis of its miscibility with both the dehydrating agent (e.g., ethanol) and the binding agent (e.g., paraffin). Such an agent may not be necessary if the dehydrating agent is miscible with the binding agent. In a common technique, the sample is infiltrated with a transitional solvent after dehydration. In a preferred embodiment, transitional solvents, such as hydrocarbon solvents that are miscible with both ethanol and paraffin, are used. The transitional solvent is then commonly removed and replaced by the embedding agent (e.g., molten paraffin) from the sample by heating the sample with or without the aid of a vacuum.

Embedding materials include paraffin, cellulose, nitrate, gelatin, agarose, epoxy resins, carbowax, and soaps. One purpose of binding agents is to confer strength and support to the arrays during sectioning. Paraffin and other waxes and resins have the additional benefit of preventing water vapors from deteriorating the constituents of the samples. "Binding agent" as used herein includes embedding materials.

Sectioning is a technique known to persons skilled in the art and it includes cutting the sample into slices. In one embodiment, the slices can be as thin as 2 µm.

The preparative stages that have been given as examples are merely samples of possible histological techniques that can be used to create histological preparations. A person skilled in the art would know that variations of these techniques exist and that various tissue and/or cell samples can be prepared using alternative techniques and methods known to persons skilled in the art. A person skilled in the art would also appreciate that different matrices and/or biopsy samples or uses thereof may necessitate the use of different preparative methods, solvents, and agents.

"Different origin" refers to the use of a type of cell and/or tissue sample to be arranged in the matrix that is different from the type of tissue comprising the matrix. Preferably, the matrix is of an origin that does not cross react with the biopsy sample(s). For instance, the tissue and/or cell samples may be of animal origin, while the matrix is comprised of processed animal tissue, or the tissue and/or cell samples may be from one species, while the matrix is comprised of tissue from another species.

"Array" as used herein refers to tissue and/or cell samples arranged in a matrix material. In one embodiment, the purpose of the array is to arrange the samples in a defined spatial orientation so that they can be identified unambiguously. In another embodiment, the purpose is to embed cell samples and to prevent deformation of cell or tissue samples during processing. In addition, the array can be used when precise orientation of tissue samples is required, such as with structures with lumen like the intestine.

"Matrix material" as used herein refers to material used as a receptacle or foundation for the processing of histological samples. In one embodiment, the matrix material provides structural integrity for the construction of the array. In another embodiment, the matrix material assists in the processing of tissues for histological preparation. The tissue matrices used in this disclosure are selected on the basis of consisting of a suitable blend of proteins, lipids, carbohydrates and water to produce a matrix with low cross-reactivity to the samples contained therein, and minimal shrinking and good cutting properties. In a preferred embodiment of the invention, the matrix material is processed animal tissue.

"Processed animal tissue matrix" as used herein and throughout this disclosure refers to one type of tissue matrix, wherein the tissue is comprised of animal tissue. One embodiment of this disclosure is a processed animal tissue matrix that can be used to create a biopsy array. The processed animal tissue used in the processed animal tissue matrix comprise a suitable blend of proteins, fat, carbohydrates and water to produce a matrix with minimal shrinking and good cutting properties. The processed animal tissue used is preferably selected on the basis that it does not shrink or collapse during dehydration, and should preferably not be so hard as to make sectioning difficult. In one embodiment, the processed animal tissue matrix used performs well in all histological preparative stages. In one embodiment of the disclosure, SPAM® is used to create the processed animal tissue matrix of the disclosure. SPAM® processed pork exhibits minimal shrinking and good cutting properties when used as a matrix material for biopsy arrays.

In one embodiment of the disclosure, a biopsy sample is obtained and fixed in a suitable fixative. The processed animal tissue matrix is preferably fixed in a similar way. The sample is arranged in the processed animal tissue matrix to create the array. The array is capped, dehydrated, passed through a transitional solvent and embedded in a binding agent.

Embodiments of this disclosure have many advantages, including greatly enhanced efficiency and speed for tissue testing; greatly decreased cost for multiple tissue testing; great economies in the use of tissue samples, reagents and testing materials; great flexibility and ease of constructing biopsy arrays; lack of need for deparaffinization and re-embedding; ability to use tissues or cells as sources of samples for the array; and the ability to use fresh, fixed or paraffinized biopsy samples. Employing a matrix during processing results in superior consistency in quality. Since all tissue biopsies can be treated simultaneously, one can reasonably expect less variation among them within the same paraffin block. In some embodiments, the disclosure also enables one to obtain serial sections (ribbons), for instance, as thin as 2 µm. In another embodiment, a biopsy array can be produced in less than 8 hours, more preferably between 8 and 24 hours. When using banked tissue (transitional solvent), an arrayed block can be generated within 3 hours for paraffin embedding, and in 10 to 15 minutes for frozen preparations.

The matrix method allows parallel processing and sectioning of small tissue samples of cylindrical shape of very small diameter by laying them horizontally by the surgeon performing the biopsies within a pre-sterilized matrix (chemically, by gamma irradiation, etc.). This is important when dealing with biopsies (e.g., prostate, thyroid, breast) when one has to report absolute and relative numbers (length/volume, percentage of malignant tissue).

In using a matrix according to the matrix method, during collection, the core biopsies are placed directly into the preformed matrix and then processed in any tissue processor or manually. Although the preformed matrix is designed for manual processing, it is compatible with all existing laboratory methods and automatic dehydration and infiltration devices. However, the use of microwave accelerated schedules of tissue processing is not recommended without prior testing. The matrix material is able to withstand exposure to all the fixatives and volatile reagents typically used in histology and will dehydrate and infiltrate in perfect "harmony" with the biopsies within it, without any distortions. Friable biopsies are protected during processing, eliminating any loss of precious diagnostic material while serial sectioning and spreading are greatly facilitated.

When dealing with prostate biopsies, the matrix is used in conjunction with rigid embedding cassettes. The matrix is aligned carefully in the paraffin block and the paraffin block is aligned carefully in the plane of sectioning. A corollary of employing a matrix during harvesting the biopsies is that even minute fragments of tissue are not lost during transportation and the potential artifacts associated with processing are completely eliminated. Since all tissue biopsies are treated simultaneously (i.e., within the same paraffin block), one can reasonably expect less variation among them.

The matrix method makes the whole process very efficient and robust and makes biopsy sectioning accessible to any average technician. The matrix ensures that the biopsies are perfectly aligned, thus allowing very precise and expeditious diagnosis. The matrix method decreases by one order of magnitude the material, time and manpower expenses for prostate core biopsy processing and analysis. However, the procedure does not impose a supplementary burden on either the clinician harvesting the tissue or the laboratory staff, including the pathologist reading and interpreting the slides, and is suitable for automated histology analysis. The burden of the pathologist is, therefore, significantly lessened (much smaller number of slides and much easier to read and quantify). The matrix method also enables-three dimensional representations of the neoplastic growth.

In another embodiment, the disclosure provides a tissue and or cell array comprising a processed animal tissue matrix. The construction of the array is flexible and allows custom biopsy arrays to be built. In one embodiment, the array is a multi-specimen array. "Multi-specimen array" includes arrays composed of different samples from a single species, the same cell or tissue type from different species, or the same cell or tissue type from the same species at different developmental times. In a further embodiment, the array is a multi-use array. "Multi-use array" includes arrays used to simultaneously screen a number of biopsy samples, to create tissue-banking systems and to manufacture sections and slides. One value of this technology is that testing can be done on many samples in a timely manner with consistency to allow for high-throughput analysis.

An additional embodiment of the disclosure provides a method for preparing the biopsy arrays comprising a processed animal tissue matrix. At least one cell or tissue sample is manipulated and positioned in a recipient receptacle in the processed animal tissue matrix. It is preferable that the receptacle in the processed animal tissue matrix is not a complete puncture through the processed animal tissue, but a thin layer of tissue remains at the bottom to create the receptacle. After the samples are arranged in the matrix, processed animal tissue matrix, preferably in the similar preparative stage as the processed animal tissue matrix, is applied to the top of the matrix and acts like a lid. In one embodiment, the samples are arranged in the matrix at any point in the histological preparation process. The sample-containing matrix can then be processed using known histological techniques.

Method for Preparing a Multi-Specimen Biopsy Array within a Matrix

The method allows for the preparation of a "multi-specimen" biopsy array. The method allows parallel processing of multiple biopsy samples of cylindrical shape and very small diameter (0.5 to 1 mm) as typically obtained during core biopsy procedures. The method disclosed herein uses a matrix in which parallel grooves were pre-made. The biopsy samples are then laid horizontally in the parallel grooves of the matrix.

The method is particularly advantageous when dealing with biopsies (e.g., prostatic, breast, thyroid) where one has to analyze multiple biopsy samples and report the percentage of malignant tissue. The present method makes the whole process quite easy and it is believed that biopsy sectioning is now accessible to any average technician. The burden of the pathologist is significantly lessened (much smaller number of slides and much easier to read and quantify). The method also simplifies the tracking of the biopsy samples, which facilitates 3-D reconstruction.

The present method is also useful for instances when a small number of biopsies (or only one) are taken. This is because by encasing the biopsy within a matrix up front, the risk of losing it in the processor, fragmentation (sometimes the tissue harvested is already brittle or friable: scars, hemorrhage, foci of necrosis, etc.) or distortion during processing is completely eliminated.

FIG. 1A is a perspective view of a matrix for receiving biopsy samples according to an embodiment of the disclosure. As shown in FIG. 1A, a matrix 100 includes a block 102 of matrix material 104. In the upper surface 106 of block 102 a plurality of parallel receptacles in the form of grooves 120*a*, 120*b*, 120*c*, 120*d*, 120*e*, and 120*f*, have been made. The grooves 120*a*-120*f* are made by machining or cutting into the upper surface 106 of block 102. The machining/cutting is relatively simple and requires less than 5 minutes per matrix for preparing 12 grooves. The machining of the matrix can be automated or performed manually.

The matrix can be prepared from a range of different materials. The material used in preferably hydrophilic and exhibits minimal distortions during dehydration, clarification with solvents and paraffin infiltration. In particular, the material preferably has similar chemical properties with the biopsy samples to be placed therein. Some plant and animal tissues can be used as the matrix material. For example, plant material (e.g., sweet potato) and animal tissues (e.g., beef liver) can be utilized to create the block. Synthetic materials having the desired properties can also be used. In preferred embodiments, the material chosen is widely available and inexpensive.

In an embodiment of the disclosure, a method is provided for preparing a suitable processed animal tissue matrix for use to embed a biopsy, such as to create a biopsy array. The processed animal tissue matrix can be prepared using histological practices and procedures known to persons skilled in the art. In one embodiment, receptacles are formed in the processed animal tissue to create the matrix. It is preferable if the receptacles are sized to accommodate the biopsy samples tightly. This aids in maintaining desired orientation of the sample within the matrix.

In a preferred embodiment, an off-the-shelf processed animal tissue product is utilized (e.g., SPAM®). This off-the-shelf processed animal tissue product material exhibited very good chemical and mechanical properties (it can be fixed, dehydrated, clarified, embedded and sectioned with ease). The matrix can be pre-stained for good optical contrast. Alternatively, the matrix is left unstained and the biopsies are pre-stained during fixation.

The block of matrix material is optionally treated before machining. For example, the block of material can be fixed, dehydrated and infiltrated with paraffin before machining them to the desired shape. After machining, the matrix can be "reverse processed" to water. That is, a solvent is applied for extracting the paraffin, ethanol is then applied for extracting the solvent, then the matrix is rehydrated with water and a fixative is applied.

In one embodiment, the following method is used to prepare the processed animal tissue material. The processed animal tissue is sectioned in slices, preferably no thicker than 10 mm to ensure good penetration with the fixative. The processed animal tissue matrix is immersed in a fixative. One fixative that can be used is fresh-buffered formalin (4% formaldehyde in 150 mM PBS-phosphate-buffered saline). It is preferable if the processed animal tissue is fixed in formalin for at least 24 hours. After the processed animal tissue material is collected and fixed, the next step is to dehydrate the processed animal tissue material. In order to dehydrate the processed animal tissue material, progressive concentrations of ethanol in water are used. The last bath is in absolute ethanol. The processed animal tissue material is preferably washed a minimum of three times with a transitional solvent. The processed animal tissue is then paraffin-embedded. A block of the material is then used for preparing a matrix. Receptacles are formed into the processed animal tissue by drilling, machining, or punching. The matrices are then reverse-processed to water/fixative by removing the paraffin with a transitional solvent, removing the solvent with ethanol, removing the ethanol with water and stabilizing the animal tissue with a fixative. Techniques for reverse-processing are known to persons skilled in the art. The matrix is ready to receive the biopsy samples to create the array.

Alternatively, machining can be performed without prior paraffin infiltration. In this method, the block of matrix material is fixed, cryo-protected with sucrose, and then frozen. Techniques for cryo-protection, freezing and sectioning of frozen histological preparations are known to persons skilled in the art. The frozen block is then machined to the desired shape of the matrix. After machining, the matrix is then thawed in fixative.

In alternative embodiments, the matrix material is molded in the desired shape and no machining is required. For example, where the matrix material is processed animal tissue, a paste of the processed animal tissue can be poured into an appropriately shaped mold. After molding, the shape of the matrix can be stabilized using heat and/or chemical fixation. The molding process thus eliminates the need for machining and simplifies manufacturing of the matrix.

Figure 1B:
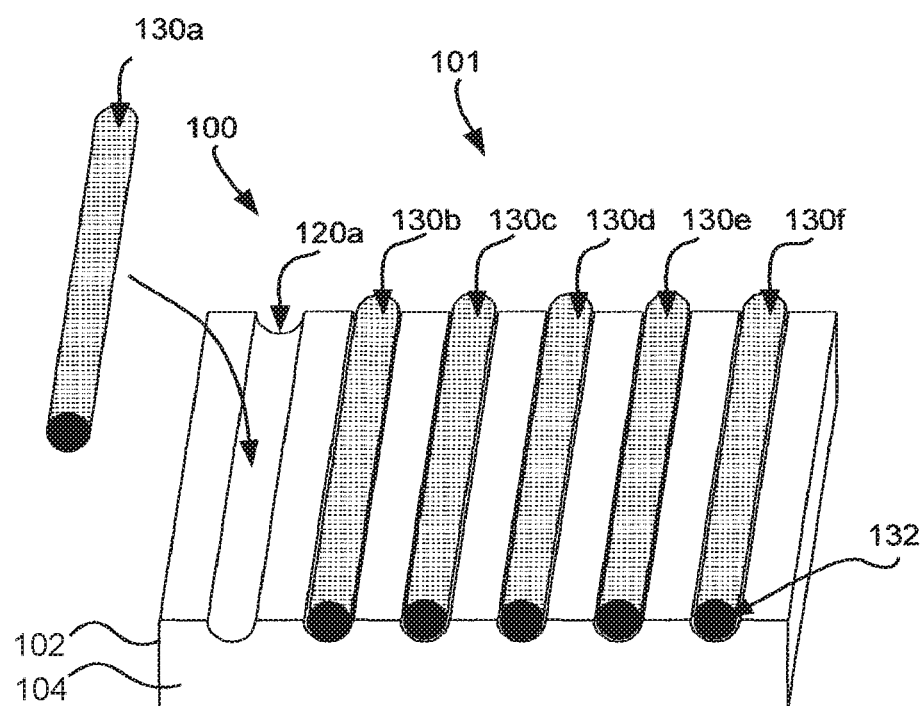
FIG. 1B illustrates the loading of biopsy samples into the matrix block of FIG. 1A.

After preparation, a matrix can either be used immediately, or stored in an appropriate fixative until required. The use of fixative for long-term storage is known to persons skilled in the art. When biopsy samples are received, a matrix is prepared or removed from storage. FIG. 1B illustrates loading of biopsy samples into the matrix block of FIG. 1A. As shown in FIG. 1B, biopsy samples 130a, 130b, 130c, 130d, 130e, and 130f are placed one by one in grooves 120a-120f of matrix 100 (see FIG. 1A) to form an array 101 of biopsy samples supported by matrix 100.

An embodiment of this disclosure is a method of obtaining and treating a biopsy sample for use in the matrix. The cell or tissue sample can be prepared using histological practices and procedures known to persons skilled in the art. For instance, the samples can be fresh, fixed or embedded in a binding agent. It is preferred that the processed animal tissue matrix and tissue and/or cell samples are in a similar preparative stage at the time the samples are arranged in the matrix, because some of the chemicals used during processing are incompatible. For example, if the biopsy sample is fresh, then the matrix should preferably also be fresh. If the biopsy sample is fixed in ethanol, then the matrix should preferably also be in ethanol. If the biopsy sample is stored in a transitional solvent, then the matrix should preferably be in a transitional solvent. If the biopsy sample is paraffin embedded, then the matrix is preferably embedded in paraffin. Alternatively, as noted below, the processed animal tissue matrix can be in a subsequent preparative stage to the tissue and/or cell sample.

As shown in FIG. 1B, the biopsy samples are preferably marked at one end with, e.g., ink (132), to identify the orientation of the sample relative to the entry point of the needle. The biopsy samples are preferably loaded into the matrix in the same orientation. The matrix itself may also be marked or shaped such that the order of the biopsy samples can also be identified.

The biopsy samples are collected and then fixed. Suitable fixatives and procedures for good quality fixation are familiar to those skilled in the art. After the tissue is collected and fixed, the next step is to dehydrate the tissue sample. In order to dehydrate the tissue sample, progressive concentrations of ethanol in water are used. The last bath is in absolute ethanol. The tissue sample is preferably washed a minimum of three times with a transitional solvent. The tissue samples can then be trimmed to fit in the matrix. If desired, it is possible to form receptacles into the matrix and the samples can be fitted into the processed animal tissue matrix during any stage. This allows significant savings in the labor involved when one has to process large numbers of samples.

In a preferred embodiment, as shown in FIG. 1B, grooves 120a-120f of matrix 100 are the same size and shape, and biopsy samples 130a-130f are also of the same size and shape. Thus, matrix 100 presents the biopsy samples at the same depth. This allows a single section of the array to intercept all of the biopsy samples (see, e.g., FIG. 1F). This reduces waste of the tissue and allows for significantly more tissue to be left in the resulting block for archival purposes.

FIG. 1C illustrates application of a sponge to the matrix block of FIG. 1A. After the biopsy samples are loaded, a sponge 140 is placed on top of the array 101 of biopsy samples supported by matrix 100 as shown in FIG. 1C. This prevents curling of the biopsy samples during processing. In alternative embodiments, a sheet of the same matrix material may be used in place of sponge 140.

In one embodiment of the disclosure, a biopsy sample is obtained and prepared. The processed animal tissue matrix is preferably in the similar or subsequent preparative stage as the samples. At least one sample is arranged in the processed animal tissue matrix to create the array. The array is then preferably capped and embedded in a binding agent.

FIG. 1D illustrates the matrix block of FIG. 1A and sponge of FIG. 1C in combination with a tissue cassette. Sponge 140 and the array 101 of biopsy samples supported by matrix 100 are then introduced in standard tissue processing cassette 150 as shown in FIG. 1D. The upper 152 and lower 154 sides of the standard tissue processing cassette 150 are typically perforated to allow passage of the reagents through the cassette 150. Loading the biopsy samples into the matrix and loading into the standard tissue processing cassette can be achieved in less than about five minutes for up to about twelve samples. The loaded tissue cassette can then be processed using standard tissue processing equipment and techniques. Preferably, the matrix is placed in the apparatus with the grooves facing upward to reduce the chance of migration of the biopsy samples. During processing, the biopsy samples and matrix are typically embedded in paraffin wax in preparation for sectioning. Processing and embedding of the loaded matrix are carefully performed in order to maintain the flatness of the matrix in order to allow for easy sectioning.

FIG. 1E is a schematic representation of a slide prepared from a section of the matrix block and biopsy samples of FIG. 1A according to an embodiment of the disclosure. After tissue processing and embedding, the embedded array 101 of biopsy samples supported by matrix 100 is sectioned in the standard fashion using a microtome. Sections can readily be cut between 2 µm and 10 µm in thickness. With the embedded array 101 of biopsy samples supported by matrix 100, sections can be obtained through the entire length of each biopsy sample in the same section, allowing single slides to be created, which allow for full-core analysis of multiple samples. The sections are placed on slides using conventional tissue processing techniques.

As shown in FIG. 1E, a slide 160 includes a section 162 under a cover slip 164. The section 160 includes full-length sections through each biopsy sample 130a, 130b, 130c, 130d, 130e, and 130f separated from one another by matrix material 104. The biopsy samples can be readily identified and distinguished from the interspersed matrix material 104. The slide allows for analysis of each of the biopsy samples 130a, 130b, 130c, 130d, 130e, and 130f along the full length of each core. FIG. 1F is a picture of a sample slide prepared utilizing the matrix block of this disclosure. The slides can be used for histological procedures, including quantitative analyses and parallel processing.

Alternative Matrix Configurations

The matrices of this disclosure can be readily manufactured in a range of shapes suitable for supporting biopsy samples. Alternative matrix designs can provide features and advantages for supporting biopsy samples. A range of alternative matrix designs is illustrated in FIGS. 2A-2D.

Figure 2A:
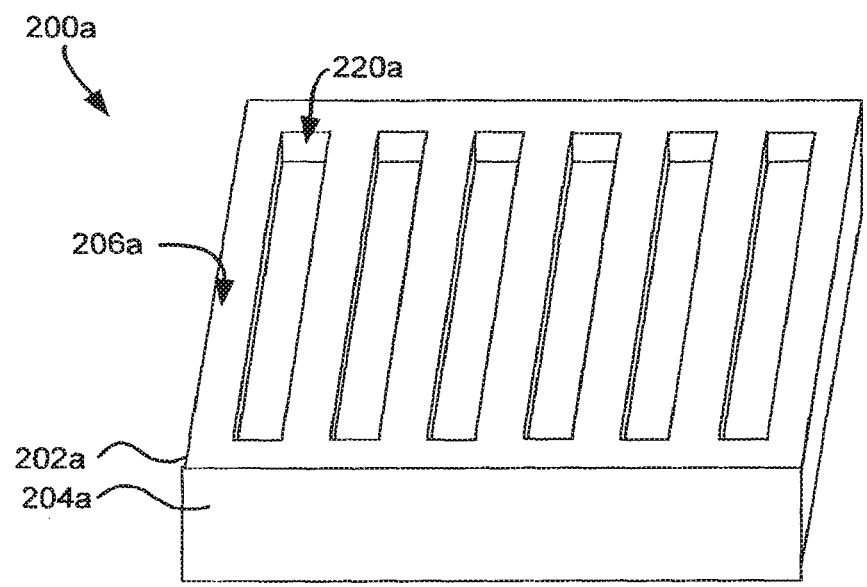
FIG. 2A is a perspective view of an alternative matrix block according to an embodiment of the disclosure.

FIG. 2A is a perspective view of an alternative matrix block according to an embodiment of the disclosure. As shown in FIG. 2A, a matrix 200a includes a block 202a of matrix material 204a. In the upper surface 206a of block 202a, a plurality of parallel receptacles in the form of grooves 220a, have been made. The plurality of grooves 220a is made by molding or machining/cutting into the upper surface 206a of block 202a. In the embodiment shown in FIG. 2A, the grooves 220a are rectangular in section and closed ended. Grooves 220a are the same size and shape. Alternatively, the grooves can be made at various depths and widths, in order to accommodate the various types of biopsies.

Figure 2B:
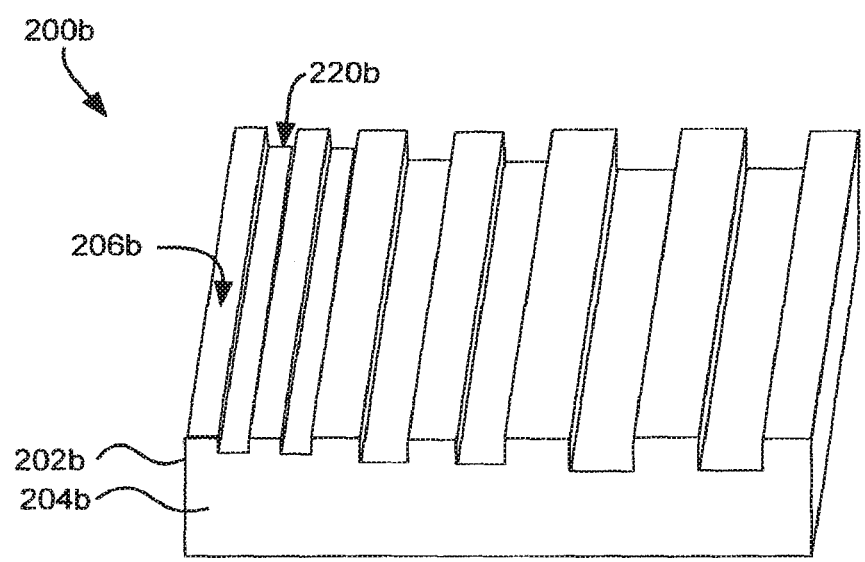
FIG. 2B is a perspective view of an alternative matrix block according to an embodiment of the disclosure.

FIG. 2B is a perspective view of an alternative matrix block according to an embodiment of the disclosure. As shown in FIG. 2B, a matrix 200b includes a block 202b of matrix material 204b. In the upper surface 206b of block 202b, a plurality of parallel receptacles in the form of grooves 220b, have been made. The plurality of grooves 220b is pre-made by molding or machining/cutting into the upper surface 206b of block 202b. In the embodiment shown in FIG. 2B, the grooves 220b are rectangular in section and open ended. The grooves 220a have different sizes to accommodate different sizes of biopsy samples while presenting them at the same height for sectioning.

Figure 2C:
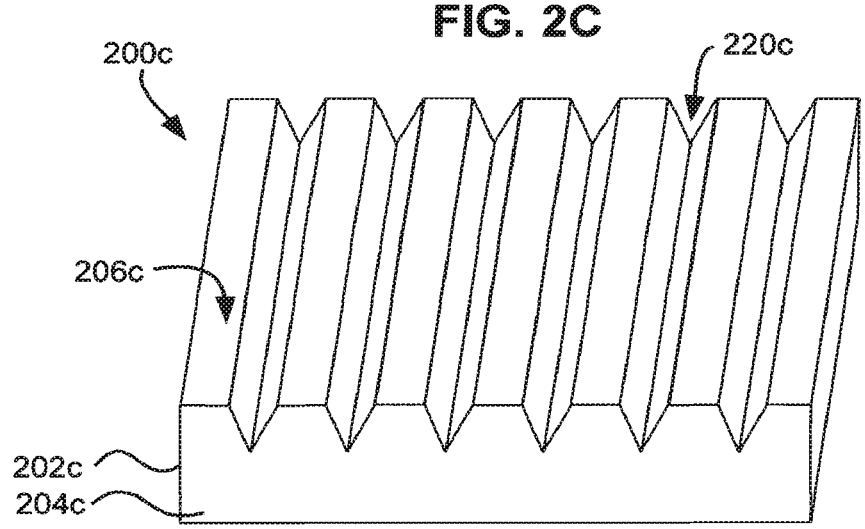
FIG. 2C is a perspective view of an alternative matrix block according to an embodiment of the disclosure.

Grooves can be prepared having a variety of different sectional shapes. For example, in an alternative variation, the grooves can have a "triangular" shape, in order to accept any size of biopsy sample. FIG. 2C is a perspective view of an alternative matrix block according to an embodiment of the disclosure. As shown in FIG. 2C, a matrix 200c includes a block 202c of matrix material 204c. In the upper surface 206c of block 202c, a plurality of parallel receptacles in the form of grooves 220c, have been made. The plurality of grooves 220c is pre-made by molding or machining/cutting into the upper surface 206c of block 202c. In the embodiment shown in FIG. 2C, the grooves 220c are triangular in section and open ended. Grooves 220c are the same size and shape. Alternatively, the grooves can be made at various depths and widths.

Figure 2D:
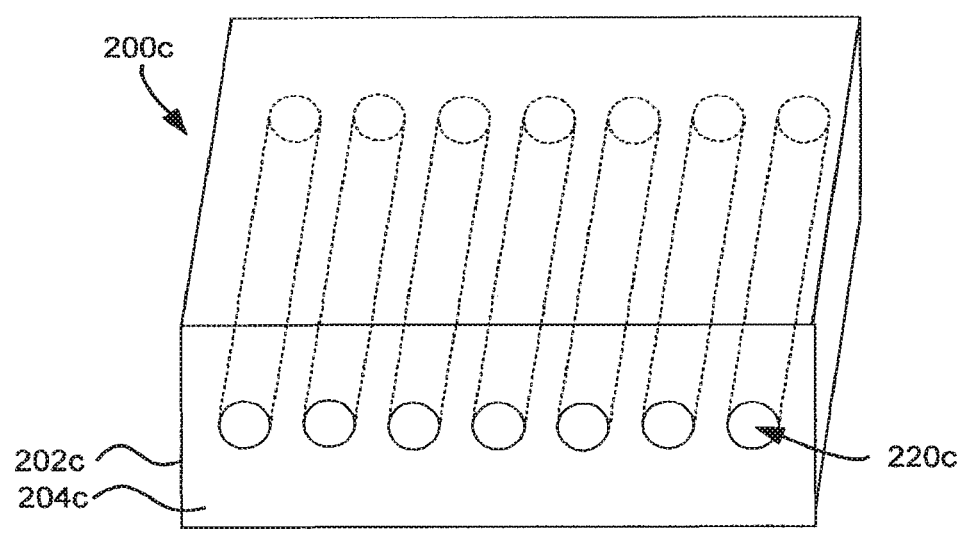
FIG. 2D is a perspective view of an alternative matrix block according to an embodiment of the disclosure.

FIG. 2D is a perspective view of an alternative matrix according to an embodiment of the disclosure. As shown in FIG. 2D, a matrix 200d includes a block 202d of matrix material 204d. In the block 202d, a plurality of parallel receptacles in the form of bores 220d, have been made. The plurality of bores 220d are pre-made by molding or machining/cutting into the block 202d. In the embodiment shown in FIG. 2D, the bores 220d are circular in section and open at both ends. Bores 220d are the same size and shape. Alternatively, the bores can be made at various depths and widths, in order to accommodate the various types of biopsies.

In order to insert biopsy samples into the matrix of FIG. 2D, the matrix 200d is placed in a rig that allows little scoops (half cylinder in shape) to be introduced through the bores 220d and protrude at least the length of the expected biopsy samples. The samples are placed in the groove of the scoop. Another half-cylinder scoop is placed as a "lid" over the biopsy and both scoops are introduced within the matrix 200d. After the correct location is reached, both scoops are extracted, leaving the biopsy samples inside the bores 220d of the matrix 200d. The matrix with the enclosed biopsies is then introduced into a tissue cassette and processed as usual. This method can be used on the operating table where the biopsies are taken. This would eliminate "chain of custody" issues. In an alternative embodiment, a "modified" biopsy needle is used to introduce the biopsy sample directly into the matrix. The biopsy needle may be single use or multiple uses. However, if the biopsy needle is to be used after introduction into the matrix, the matrix is required to be sterile and the matrix material must be biocompatible to avoid contaminating the needle.

In alternative embodiments, individual biopsy samples are mounted within individual matrices of identical external shape and size. The matrices can have different size grooves/bores for receiving the biopsy samples so long as the samples are presented in the same plane. The individual matrices can be processed separately and then grouped in various combinations during embedding. The identical size of the matrices would allow the resulting composite block to have all biopsies located in the same plane of sectioning.

Alternative Matrix Configuration and Loading Apparatus

Figure 3A:
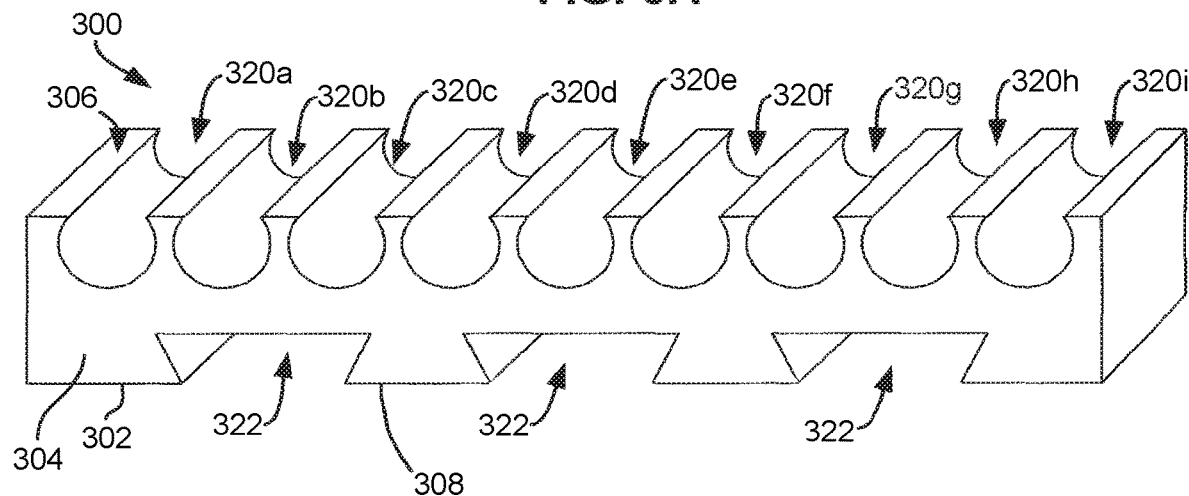
FIG. 3A is a perspective view of an alternative matrix block according to an embodiment of the disclosure.
Figure 3B:
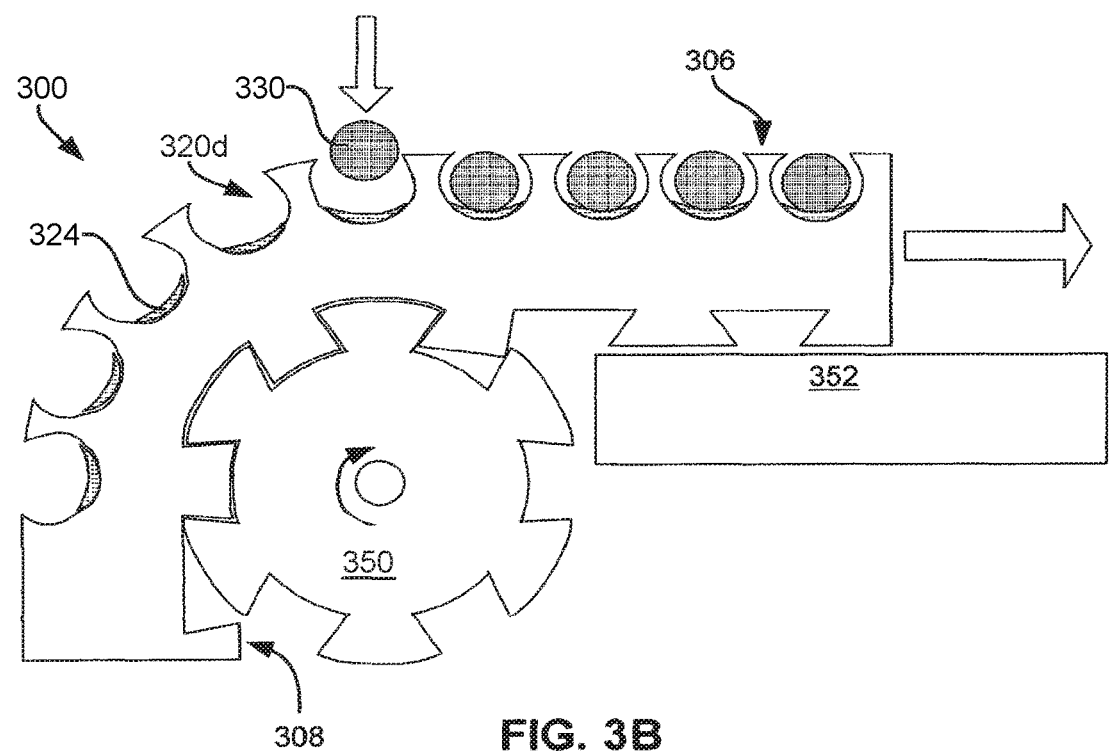
FIG. 3B is a schematic view of a method and apparatus for loading biopsy samples into the matrix block of FIG. 3A according to an embodiment of the disclosure.
Figure 3C:
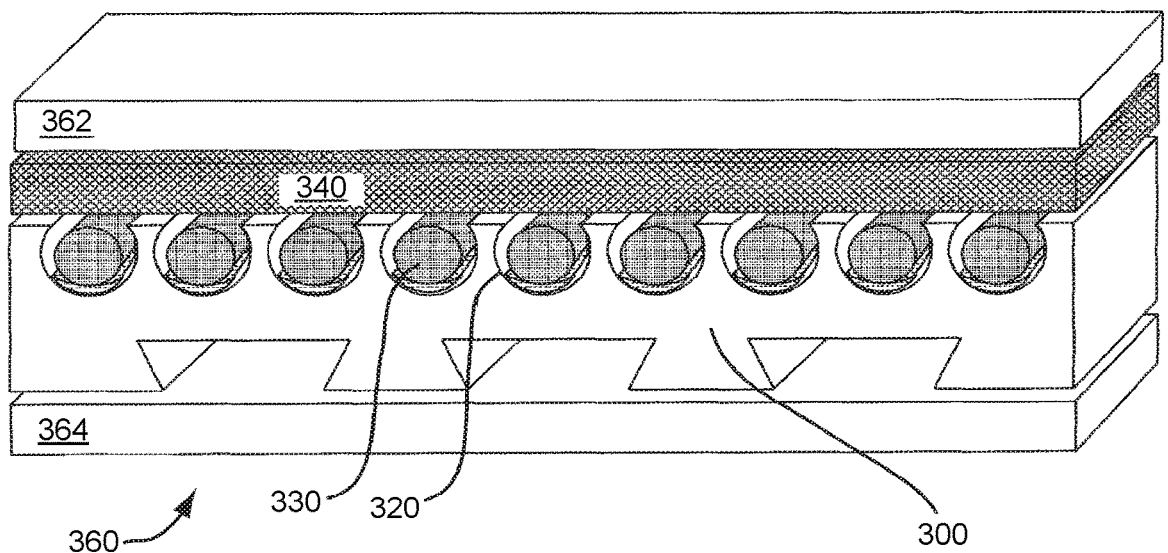
FIG. 3C illustrates the matrix block of FIG. 3A in combination with a tissue cassette and sponge.

One advantage of the matrix material of this disclosure is that the material is relatively flexible. The matrix material has a certain degree of flexibility when hydrated. The flexibility of the material allows the design of matrix configurations that facilitate the loading and securing of biopsy samples within the matrix. As shown in FIGS. 3A-3C, a matrix can be prepared having channels provided with a small opening/slot to the upper surface. To load biopsy samples, the matrix is placed over a curved surface. This causes the openings to be enlarged to facilitate the introduction of the biopsy sample. For example, the biopsy needle can be used to introduce the sample directly to the matrix. After introduction of the sample, the matrix is straightened, such that the opening diminishes in size, securing the sample in place. When the needle is extracted, it will leave the biopsy behind.

FIG. 3A is a perspective view of an alternative matrix block according to an embodiment of the disclosure. As shown in FIG. 3A, a matrix 300 includes a block 302 of matrix material 304. In the upper surface 306 of block 302, a plurality of parallel receptacles in the form of channels 320a, 320b, 320c, 320d, 320e, 320f, 320g, 320h, and 320i have been made. The channels 320a-320i are made by cutting, machining or molding the upper surface 306 of block 302. As shown, the channels 320a-320i have a narrow opening/slot through the upper surface 306. The lower surface 308 is provided with a plurality of features 322 in the form of dovetail slots.

FIG. 3B is a schematic view of a method and apparatus for loading biopsy samples into the matrix block of FIG. 3A according to an embodiment of the disclosure. The matrix material has a degree of flexibility when hydrated. As shown in FIG. 3B, features 322 are engaged with a roller 350. Roller 350 forces matrix 300 into a curved shape. The curved shape of matrix 300 increases the size of the openings of channels 320a-320i. A plurality of biopsy samples 330 is introduced into the plurality of channels 320a-320i while the openings of the channels 320 are enlarged. As the channels 320a-320i are sequentially loaded, matrix 300 moves over roller 350 onto platform 352. Matrix 300 straightens out on platform 352, causing the openings of channels 320a-320i to become smaller, thereby trapping biopsy samples 330 within channels 320a-320i. Optionally, an adhesive/sticky material 324 can also be provided in channels 320a-320i to further secure biopsy samples 330. One example of adhesive/sticky material that can be used for securing the biopsies in place is a dilute solution of gum Arabic. Other adhesive materials are known to those skilled in the art.

Figure 3D:
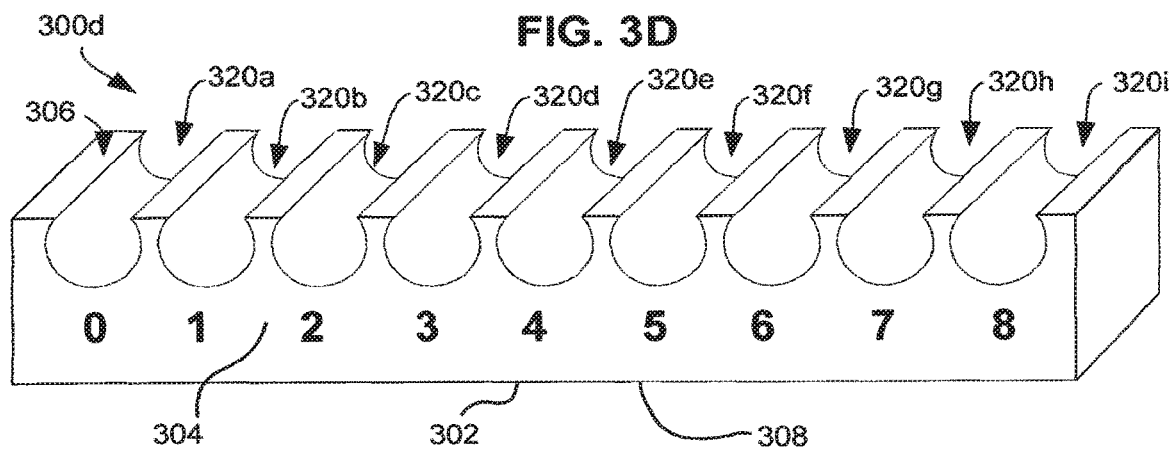
FIG. 3D is a perspective view of a variation of the alternative matrix block of FIG. 3A according to an embodiment of the disclosure.

After loading of the biopsy samples 330, the matrix 300 and biopsy samples 330 are processed as previously described. FIG. 3C illustrates the matrix block of FIG. 3A in combination with a tissue cassette and sponge. A sponge 340 is placed on top of matrix 300, and the matrix 300, sponge 340 and biopsy samples 330 are then introduced in standard tissue-processing cassette 360 as shown in FIG. 3D. The upper 362 and lower 364 sides of the standard tissue-processing cassette 360 are typically perforated to allow passage of the reagents through the cassette 360.

The loaded tissue cassette can then be processed using standard tissue-processing equipment and techniques. Preferably the matrix is placed in the apparatus with the grooves facing upward to reduce the chance of migration of the biopsy samples. During processing, the biopsy samples and matrix are typically embedded in paraffin wax in preparation for sectioning. Processing and embedding of the loaded matrix are carefully performed in order to maintain the flatness of the matrix in order to allow for easy sectioning.

FIG. 3D is a perspective view of a variation 300d of matrix block 300 of FIG. 3A, according to an embodiment of the disclosure. As shown in FIG. 3D, a matrix 300d includes a block 302 of matrix material 304. In the upper surface 306 of block 302 a plurality of parallel receptacles in the form of channels 320a, 320b, 320c, 320d, 320e, 320f, 320g, 320h, and 320i have been made. The channels 320a-320i are made by cutting, machining or molding the upper surface 306 of block 302. As shown, the channels 320a-320i have a narrow opening/slot through the upper surface 306. The lower surface 308 is not, in this case, provided with dovetail slots.

Alternative Tissue Matrix Material

In an alternative embodiment, a versatile synthetic tissue matrix for handling, processing and sectioning multiple biopsies or explants is synthesized from various ingredients as specified below. The composition of the synthetic tissue matrix is essentially a "man-made meat/tissue." The synthetic tissue matrix is made by combining: 2% to 14% animal protein (preferably myofibrillar, e.g., pork, chicken, or fish surimi); 0.1% to 5% Animal fat; 2% to 15% Vegetable oil (e.g., palm, corn, sunflower, olive); 2% to 15% Glycerin; 1% to 10% antifoaming agent (e.g., agarose, etc.); and inorganic buffers: e.g., phosphate: 10-600 mM. In a preferred embodiment, the synthetic tissue matrix is made by combining: 2% animal protein (preferably myofibrillar, e.g., surimi); 5% Animal fat; 5% Vegetable oil (e.g., palm, corn, sunflower, olive); 5% Glycerin; 5% antifoaming agent (e.g., agarose); and 200 mM inorganic phosphate buffer.

The mixture is thermally gelled by heating at 60° C. to 95° C., more preferably 65° C. to 80° C., or enzymatically by using transglutaminase. These methods for gelling animal proteins are known to persons skilled in the art. Alternatively, complex carbohydrates are included for gelling (e.g., alginate, carrageenan, konjac gum, etc.), which can be ionically gelled (Ba, Zn, Ca, Sr, etc.—as salts: CaCl2, BaCl2, ZnSO4, etc.) by submerging the mixture in a water-based solution containing the salts in a concentration of 0.2% to 15%, preferably 2% to 5%. Alternatively, by incorporating in the mixture one or more of the various divalent cations (typically Ca), they are slowly released and the gel is formed within minutes of mixing. Other methods known in the art for creating gels can also be used for gelling the synthetic tissue matrix disclosed above. The ratios of the various components (proteins, lipids, carbohydrates) of the gelling mixture can be adjusted for mimicking the type of tissue to be sectioned. It is preferred that the synthetic tissue matrix be as hard, or slightly harder, than the tissue of interest. When used for analysis of biopsy samples, the material can be referred to as HISTOSPAM matrix material.

The protein gel can be maintained in viscous form for extended periods of time and gelled when needed. In an alternative embodiment, when rapid diagnosis is desired, the biopsy or explants (e.g., skin, gastric, breast) can be positioned and included in a mass of the viscous protein gel with a composition suitable for the tissue of interest, oriented as needed and the whole assembly (biopsy and surrounding protein gel) is polymerized by spraying/immersion with a crystalloid solution as previously described (Ba, Zn, Ca, Sr, etc.—as salts: CaCl2, BaCl2, ZnSO4, etc., in a water-based solution containing the salts in a concentration of 0.2% to 15%, preferably 2% to 5%). The "solidified" assemblies (biopsy plus gelled proteic mixture) can be further snap-frozen for cryosectioning and histodiagnostics. The techniques for snap-freezing, cryosectioning and histodiagnostics are well known to persons skilled in the art. Alternatively, the "solidified" assemblies (biopsy plus gelled proteic mixture) can be further chemically fixed, dehydrated, infiltrated in paraffin, sectioned and used for histodiagnostics. The techniques for chemical fixation, dehydration, paraffin infiltration, sectioning and histodiagnostics are well known to persons skilled in the art. In yet another embodiment, the protein gel can be molded, extruded or injected for creating permanent (gelled) matrices. The matrices can be frozen or chemically fixed for later use. They can also be chemically sterilized or gamma-irradiated for long-term storage. Additionally, pre-made matrices already embedded in paraffin can be machined and shaped as recipient blocks for accepting paraffin-embedded tissue fragments extracted from donor blocks. Typically, the gelled matrix is formed or shaped such that it provides pre-made receptacles for receiving the biopsies or explants (e.g., skin, gastric, breast) as disclosed above. The shape of the pre-formed receptacles within the matrix is selected based on the shape of the tissue sample to be processed: rounded or rectangular grooves for cylindrical shapes; tru-cut biopsies (prostate, breast, thyroid, gauge 20 and larger), or for fine-needle aspirates; or freeform for irregular tissue samples. The biopsies or tissue fragments can be laid horizontally (biopsy chip) or vertically. Another shape of the pre-made matrix is similar with a brush-shape or funnel-shape suitable for irregular-sized tissue fragments (tumor margins, shavings in Mohs surgery, etc.), thereby allowing the irregular fragments to be easily positioned in the appropriate angle. Once positioned in the premade receptacles, the biopsies or explant samples can be sectioned in a cryostat (for "real-time" diagnostic: breast, skin) or fixed and processed through paraffin as described above.

One other application benefiting from the multiplex sectionable matrix is for the stereotaxic mapping of large tissue/tumors/organs removed during surgery. The rule is to embed and section the fragment either in toto, or only partially, but using a systematic approach in selecting the areas to be examined (to decrease the workload but keeping at a minimum the risk of missing cancer).

First Example

The aim of the study was to assess the suitability and effectiveness of our new method of prostate biopsy collection, processing and analysis using the grooved matrix block as disclosed herein within a pilot trial, as well as to start a comprehensive tissue archive for further multi-center prospective longitudinal cohort studies.

Figure 4A:
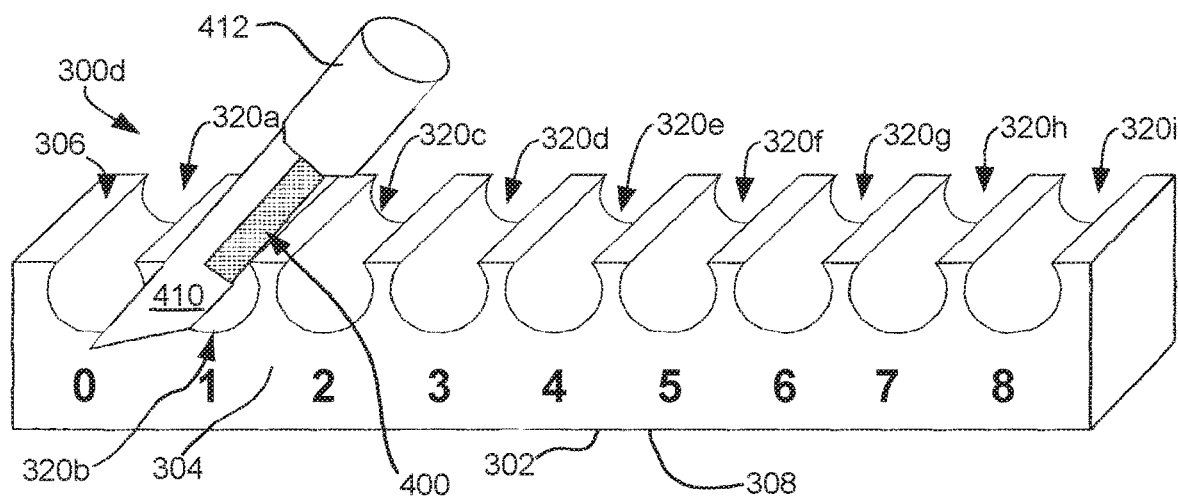
FIG. 4A is a perspective view of an alternative matrix block according to an embodiment of the disclosure.
Figure 4B:
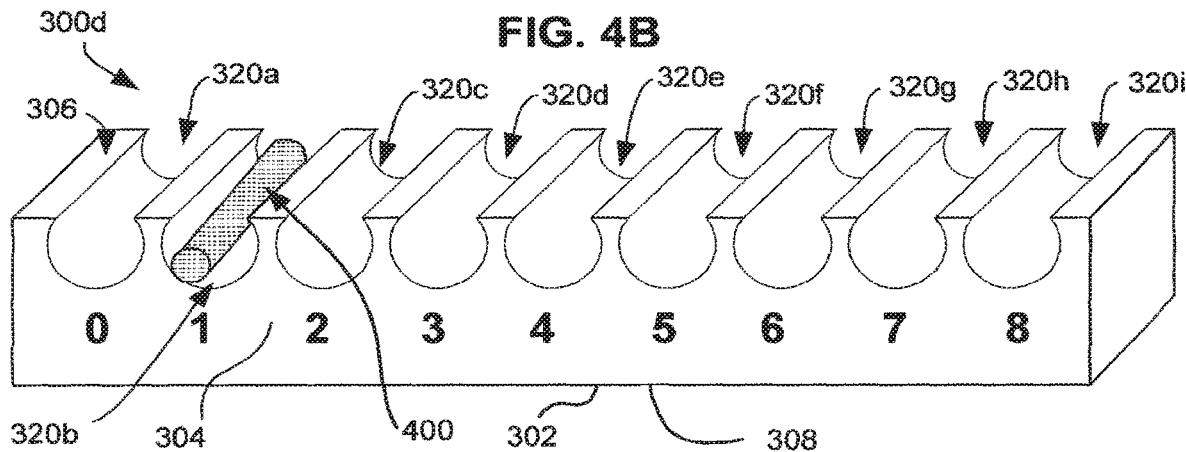
FIG. 4B is a perspective view of an alternative matrix block according to an embodiment of the disclosure.
Figure 4C:
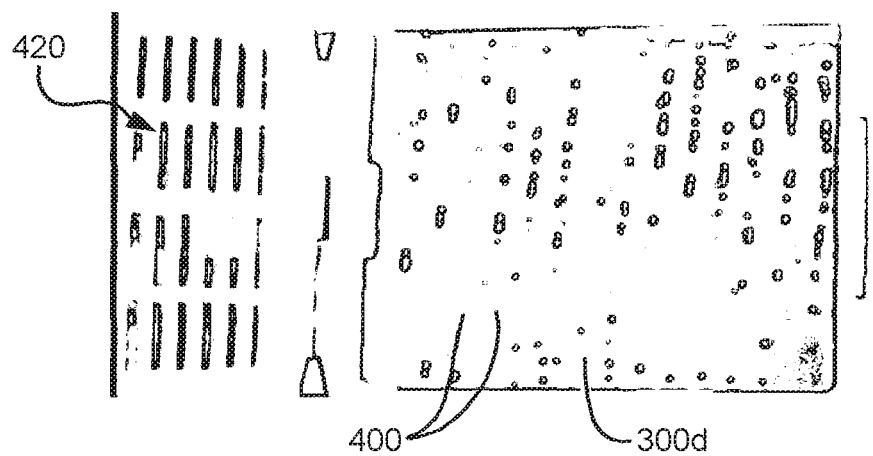
FIG. 4C shows a plurality of biopsy cores loaded in a matrix block.

Method: A multiplex grooved matrix block 300d as disclosed herein was constructed from a protein gel (see FIG. 3D) and used for aligning the specimens by the urologist who collected the biopsies from 30 patients suspected of prostate cancer. Inclusion criteria for participants in the trial were based on clinical (positive DRE) or biochemical (PSA>2.5 ng/ml) suspicion of prostate cancer. Up to 12 biopsy cores per patient (gauge 18) were collected with an ultrasound-guided biopsy gun in a single matrix and placed in a matrix 300d as shown in FIGS. 4A-4C. As shown in FIG. 4A, the biopsy core 400 was exposed at the tip of the needle 410 of the biopsy gun 412. As shown in FIG. 4B, the biopsy core 400 was deposited in a groove (320a-320i) of the matrix 300d by a gentle in-axis rotation of the needle 410. The loaded matrix was labeled and placed between two foam biopsy pads in a standard histology cassette (see, e.g., FIG. 3C), immersed in neutral-buffered formalin, and sent to the pathology department. The individual cores were placed in matrix 300d at specified positions and in the same orientation with respect to the entry point of the biopsy needle into the prostate. The location of each core 400 was marked with a number on a prostate diagram map for each biopsy protocol sheet, allowing unambiguous and easy location of the tumor and estimation of its size and extension.

Processing of biopsy-loaded matrices was performed in a standardized fashion, and consisted in: fixation for 24±2 hours with 4% formaldehyde, dehydration in graded ethanols, clearing through transitional solvents, infiltration and embedding in paraffin. Semi-serial sections at 4-5 µm were mounted on positively charged glass slides. Every fifth section was stained with hematoxylin-eosin (HE). When needed, immunohistochemistry (IHC) was performed with PIN cocktail containing mouse anti-p63 and rabbit anti-P504S (Alpha-Methylacyl-CoA Racemase or AMACR) primary antibodies at dilution 1:100 (CO001K-05—Zytomed Systems, Berlin, Germany) and visualized with Envision Flex™/HRP and DAB+(DAKO, Glostrup, Denmark).

The main outcome measures were the aggregated lengths of biopsy core fragments on slides at different levels and of the remaining tissue in the paraffin blocks; the time and material expenses for histopathology and immunohistochemistry using our new approach compared to the classical procedures.

Figure 4D:
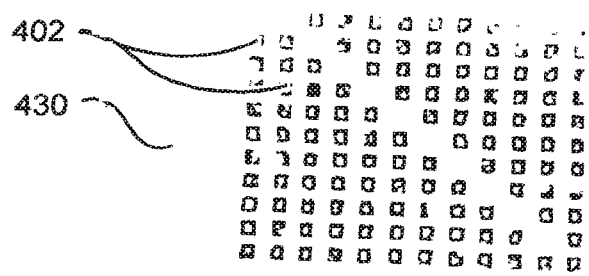
FIG. 4D shows a grid array of biopsy cores prepared for histological analysis.
Figure 4E:
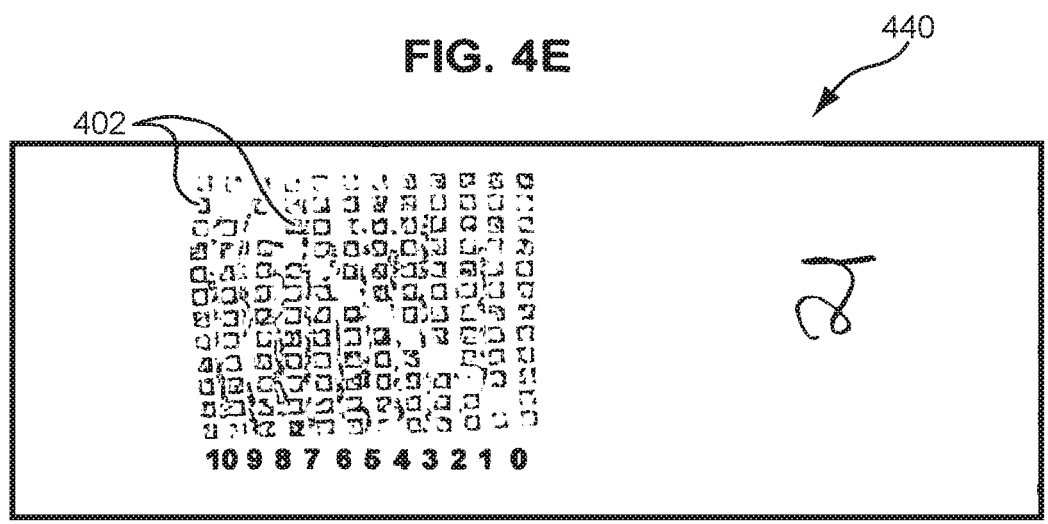
FIG. 4E shows a grad array of biopsy cores prepared for histological analysis.

Results and limitations: The results of the study are illustrated by FIGS. 4C-4E. FIG. 4C shows a plurality of biopsy cores 400 loaded in a matrix block 300d. The loaded matrix block 300d is shown in processing cassette 420. FIG. 4D shows a grid array of sections 402 of biopsy cores 400 in a paraffin block 430. For each patient, 22 semi-serial sections were cut and the remaining material was left in the paraffin block 430). The sectioning time for each paraffin block (i.e., patient), regardless of the number of biopsy cores within, did not exceed 15 minutes. FIG. 4E shows a grid array of sections 402 of biopsy cores 400 on a slide 440 prepared for histological analysis. Note that, as shown in FIG. 4E, more than 100 sections are arrayed on a single microscope slide at a density of 20 or more sections per cm².

The biopsies did not curl and maintained their correct position, even when they were fragmented at the time of placement into the matrix. The average length (±SD) of processed biopsy cores was 13±4 mm (n=299). The average aggregate length of biopsy fragments per patient (±SD) was: 131.9±25.3 mm for 10 cores (n=27), 130.0±9.1 mm for 12 cores (n=2), and 99 mm for 6 cores (n=1). The biopsies did not show curling during processing, remained properly oriented, and maintained intact tissue relationships even when the cores were fragmented. The aggregate core length was approximately 80% of the fresh core length, however, this likely represents normal core shrinkage during processing; hence, substantially all of the core was represented in the sectioned sample. Sectioning was greatly facilitated by the matrix employed and at least 50% of the bioptic material was saved in the paraffin block. Reporting of the histopathological findings was made in a quantitative fashion, and spatial representations of the neoplastic tissue were recorded.

From the 30 patients included in this study, three presented benign prostate hyperplasia (BPH), four atypical small acinar proliferation (ASAP), two intraepithelial neoplasia (PIN), one ASAP and low-grade PIN, seventeen prostate adenocarcinoma, one nonspecific nodular chronic inflammatory disease, and two were found free of prostate disease. The average length of cancer regions per patient (±SD) was 26.0±26.8 mm. A complete biopsy core was reconstructed from multiple microscope fields at ×10 magnification from two sections 5 µm apart stained with HE and PIN cocktail, respectively. Other sections from the same patient presented atypical cribriform glandular patterns suggestive of high grade PIN at three magnifications (×10, ×20, ×40) (FIG. 2, lower row), with ductal epithelial cells positive for AMACR (cytoplasmic) and negative for p63 (nuclear).

The study found a statistically significant positive correlation between PSA levels and the numbers of positive cores for each patient (r=0.580, p=0.00097, n=29), a correlation between PSA and Gleason scores (r=0.409, p=0.116, n=16), and a negative correlation between prostate volumes, as estimated via TRUS, and numbers of positive cores (r=−0.256, p=0.181, n=29), although the latter two were not statistically significant. There were statistically significant associations between positive/negative DRE and TRUS or presence/absence of prostate cancer (p=0.000203 and p=0.00298, respectively, one-tailed Fisher exact test), while TRUS was not significantly associated with prostate cancer (p=0.5535, one-tailed Fisher exact test). The volume of cancer, computed from the percentages of positive areas on biopsy cores, was correlated with PSA levels (r=0.825, p<0.0001, n=16), number of positive cores (r=0.567, p=0.022, n=16) and Gleason scores (r=0.484, p=0.05741, n=16), while the total prostate volume was not.

Conclusions: The tissue matrix employed in arraying the tissue biopsies performed flawlessly. This matrix method conferred superior speed and reliability, while reducing laboratory expenses significantly. Reading the slides was regarded by the pathologists as straightforward and accurate, particularly regarding annotations and review of suspicious areas. This technique does not require any changes in the processing schedules; paraffin blocks can be obtained without any difficulty and serial sections (ribbons) as thin as 3 μm can be obtained fairly easily. As customary, when dealing with prostate biopsies, one has to align carefully the plane of sectioning. A corollary of employing a matrix during harvesting the biopsies is that even minute fragments of tissue are not lost during transportation and the potential artifacts associated with processing are completely eliminated. Since all tissue biopsies are treated simultaneously (i.e., within the same paraffin block), one can reasonably expect less variation among them.

The multiplex method of harvesting, processing and reporting of prostate biopsies using the tissue matrix disclosed herein is an easily applicable, cost-effective method, provides tumor location information and creates consistent duplicate arrays for analysis and research purposes. Unlike other methods, it can be used efficiently for parallel quantitative analysis of various biopsy samples.

Comparative Example

A study was conducted to evaluate multiplex processing and analysis using a matrix block as disclosed herein in comparison to conventional techniques. Thirty-six patients suspected of prostate cancer were randomly assigned in two groups (conventional and matrix block) and up to 24 biopsy cores per patient (gauge 18) were collected with an ultrasound-guided biopsy gun. The biopsies were collected in separate vials and processed individually for the first 17 patients while the following 19 were collected and processed in groups of six biopsies by using the matrix block. All histopathology processing, sectioning and staining maneuvers, the yield of bioptic material examined, as well as reading the slides, were timed and recorded.

Results: The duration of harvesting the biopsies was similar using both methods (8.3 vs. 7.64 minutes). Significant savings were recorded in terms of total processing time (105.0 minutes per patient for conventional vs. 20.03 for matrix block) while the duration of reading the slides was unaffected (21.6 vs. 22 minutes). Unlike conventional methods, the matrix block maintained intact tissue relationships even when the cores were fragmented. On average, the length of the cores obtained (and examined) on slides was 66.4% of the initial biopsy (8.6/13.0 mm) when using the matrix block vs. 52.5% when conventional methods were employed (6.4/12.2 mm). Reporting of the histopathological findings was made in a quantitative fashion, and spatial representations of the neoplastic tissue were recorded.

Conclusions: The multiplex method of harvesting, processing and reporting of prostate biopsies using a matrix block as disclosed herein is an easily applicable, cost-effective method, provides tumor location information and creates consistent duplicate arrays for analysis and research purposes. Unlike other methods, it can be used efficiently for parallel quantitative analysis of various biopsy samples.

All publications, patents and patent applications are herein incorporated by reference in their entirety to the same extent as if each individual publication, patent or patent application was specifically and individually indicated to be incorporated by reference in its entirety.

The foregoing description of preferred embodiments of this disclosure has been provided for the purposes of illustration and description. It is not intended to be exhaustive or to limit the disclosure to the precise forms disclosed. Many embodiments were chosen and described in order to best explain the principles of the disclosure and its practical application, thereby enabling others skilled in the art to understand the disclosure for various embodiments and with various modifications that are suited to the particular use contemplated. It is intended that the scope of the disclosure be defined by the claims and their equivalents.

What is claimed is:

1. A method of processing biopsies, the method comprising:
    positioning a tissue sample within a mixture comprising:
        2-14% w/v animal protein;
        2.1-20% w/v one or more lipids selected from the group consisting of animal fat and vegetable oil;
        2-15% w/v glycerin;
        water;
        a gelling agent that is configured to be gelled; and
        an inorganic buffer in a concentration in the range of from 10 to 600 mM; and
    polymerizing the mixture with the tissue sample therein.

2. The method of claim 1, wherein polymerizing the mixture with the tissue sample therein comprises exposing the mixture with the tissue sample therein to a crystalloid solution.

3. The method of claim 2, wherein exposing the mixture with the tissue sample therein to a crystalloid solution comprises exposing the mixture with the tissue sample therein to a water-based solution containing a salt in a concentration of 0.2-15% w/v.

4. The method of claim 3, wherein exposing the mixture with the tissue sample therein to a water-based solution containing a salt in a concentration of 0.2-15% w/v comprises exposing the mixture with the tissue sample therein to a water-based solution containing a salt comprising one or more of Ba, Zn, Ca, Sr, $CaCl_2$, $BaCl_2$, or $ZnSO_4$, in a concentration of 0.2-15% w/v.

5. The method of claim 3, wherein exposing the mixture with the tissue sample therein to a water-based solution containing a salt in a concentration of 0.2-15% w/v comprises one or more of spraying the mixture with the water-based solution or immersing the mixture within the water-based solution.

6. The method of claim 1, further comprising freezing the mixture with the tissue sample therein.

7. The method of claim 1, wherein polymerizing the mixture with the tissue sample therein comprises enzymatically gelling the mixture using transglutaminase.

\* \* \* \* \*